United States Patent [19]
Alatossava et al.

[11] Patent Number: 5,849,488
[45] Date of Patent: Dec. 15, 1998

[54] DNA-SEQUENCE-BASED DIAGNOSIS OF MASTITIS FROM A MILK SAMPLE

[75] Inventors: Jouko Tapani Alatossava; Päivi Tuulikki Forsman; Anu Kyllikki Tilsala-Timisjärvi, all of Oulu, Finland

[73] Assignee: Oulutech Ltd., Oulu, Finland

[21] Appl. No.: 607,384

[22] Filed: Feb. 27, 1996

[51] Int. Cl.$^6$ ............... C12Q 1/68; C12P 19/34; C07H 21/02; C07H 21/04
[52] U.S. Cl. ........... 435/6; 435/91.2; 435/91.1; 536/24.3; 536/24.33; 536/23.1
[58] Field of Search ............ 435/6, 91.2, 91.1; 536/23.1, 24.3, 24.33

[56] References Cited

U.S. PATENT DOCUMENTS 5,536,638  7/1996  Rossau et al. ..................... 435/6

FOREIGN PATENT DOCUMENTS

| | | |
|---|---|---|
| 0 452 596 A1 | 10/1991 | European Pat. Off. . |
| 0 527 628 A1 | 2/1993 | European Pat. Off. . |
| 90788 | 12/1993 | Finland . |
| WO 92/00317 | 1/1992 | WIPO . |
| WO 96/002968 | 1/1996 | WIPO . |

OTHER PUBLICATIONS

Barry, T., et al, *Research*, 1:51–56 (1991) by Cold Spring Harbor Laboratory Press ISSN 1054–9803/91, PCR Methods and Applications, "The 16s/23s Ribosomal Spacer Region as a Target for DNA Probes to Identify Eubacteria".

T. Lam, et al, *Am. J. Vet. Res.*, vol. 57, No. 1, Jan .1996, pp. 39–42, "Epidemiological characteristics of bovine clinical mastitis caused by Staphylococcus aureus and Escherichia coli studied by DNA fingerprinting".

W. Zneifel, et al, *Zentralblatt Für Hygiene Und Umweltmedizin*, vol. 192, No. 6, Mar. 1992, pp. 544–553, XP000675359, "Adaption of Two Commercially Available DNA Probes for the Detection of *E. coli* and *Staphylococcus aureus* to Selected Fields of Dairy Hygiene—An Exemplary Study".

B.E. Gillespie, et al, *Journal of Dairy Science*, vol. 78, No. suppl. 1, 25 Jun. 1995, p. 172 XP000674569, "Polymerase chain reaction–based DNA fingerprinting method for identification of Streptococcus species isolated from bovine milk", See Abstract p. 63.

R.W. Bentley, et al, *Journal of clinical Microbiology*, vol. 31, No. 1, Jan. 1993, pp. 57–60, XP 000675362, "Development and Use of Species–Specific Oligonucleotide Probes for Differentiation of *Streptococcus uberis* and *Streptococcus parauberis*".

*Database WPI*, Week 9347, Derwent Publications Ltd., London, GB; AN 93–370751, XP002032801, & FI 9 201 046 A (Futekno oy), 12 Sep. 1993, see abstract.

*Primary Examiner*—W. Gary Jones
*Assistant Examiner*—Dianne Rees
*Attorney, Agent, or Firm*—Nixon & Vanderhye P.C.

[57] ABSTRACT

A rapid method for diagnosing mastitis is described. The method is based on DNA sequence identification comprising the steps of determining the presence of the following DNA sequences in a milk sample: a DNA sequence specific for somatic cells for indicating inflammation; a DNA sequence specific for a mastitis pathogen for indicating infection; and a DNA sequence specific for an antibiotic-resistance-encoding gene of a pathogen for assisting a proper drug therapy. Test kits and genus- or species-specific oligonucleotides and their use in said method are also described.

13 Claims, 7 Drawing Sheets

Fig. 2A 16S-23S rRNA intergenic spacer sequences of important bovine mastitis bacterial species (GenBank Accession number of the sequence in parenthesis)

*Streptococcus agalactiae* ATCC 27956 16S-23S intergenic spacer sequence (U39765) SEQ ID NO 1

CTAAGGATAAGGAAACCTGCCATTGCGTCTCTGTTTAGTTTTGAGAGGTCTTGTGGGCCTTAGCTCAGCTGGGA
GAGCGCCTGCTTTGCACGCAGGAGGTCAGCGGTTCGATCCCGCTAGCTCCATTGAATCGAAAGGTTCAAATTGT
TCATTGAAAATTGAATATCTATATCAAATTCCACGATTCTAGAAATAGATTGTAGAAAGTAACAAGAAATAAACC
GAAACGCTGTGAATATTTAATGAGTTTCTAGTTTTAAAGAAACTAGGTTAATAA(*GGTTAAGTTA*)
spacer(*23S*)

*Streptococcus bovis* ATCC 27960 16S-23S intergenic spacer sequence (U39766) SEQ ID NO 2

CTAAGGATAAACGGAAGCACGTTTGGGTATTGTTTAGTTTTGAGAGGTCTTGTGGGCCTTAGCTCAGCTGGGAG
AGCGCCTGCTTTGCACGCAGGAGGTCAGCGGTTCGATCCCGCTAGCTCCATTGAATCGAAAGATTCAAAGATTG
TCCATTGAAAATTGAATATCTATATCAAATTCCACGATTCAAGAAATTGTAGATAGTAACAAGAAATAAA
CCGAAAGCGCTGTGATTTAATGAGTTTAAGGTCAACAGAACCAAAATAA(*GGTT*)
spacer(*23S*)

Fig. 2B

Streptococcus dysgalactiae Lancefield's Group C, ATCC 27957 16S-23S intergenic spacer sequence (U39767) SEQ ID NO 3

CTAAGGAAATGGAACACGTTAGGGTCGTCTCTTATTAGTTTTGAGAGGTCTGTGTGGGCCTTAGCTCAGCTGGGAG
AGCGCCTGCTTTGCACGCCAGGAGGTCAGCGGTTCGATCCCGCTAGGCTCCATTAGGATAGAGATATCCTAAAAAC
TGTCCATTGAAAATTGAATATCTATATCAAATTCCACGATCAAGAAATTGATTGTACGAATAGTAACAAGAAAAT
AAACCGAAAACGCTGAATAATCAAGAGTTTTTCTAGTTAAGATATACTAGTAAAAGATAA

Streptococcus uberis ATCC 27958 16S-23S intergenic spacer sequence (U39768) SEQ ID NO 4

CTAAGGATAAGGAACACGTTGGTTAAGTCTTATTTAGTTTTGAGAGGTCTTGCAAGACGCAGAGACAAACTGTGG
GGCCTTAGCTCAGCTGGGAGAGCGCCTGCTTTGCACGCAGGAGTCAGCGGTTCGATCCCGCTAGGCTCCATAGG
ATACAGTTCAACTGAACTAATAGAAGTGAAGTTTCATTGTATCTTAGTATAGTCCATTGAAAATTGAATATCTA
TATCAAATTCCACGATCATGAAAATGATTGTAGAAAGTAACAAGAATAAACCGAAAAAAACGATAAACGCGA
ACATATTAAAAAAATCAAGAAGGTCTAAGGACTGGAAATAA

Fig. 2C

Staphylococcus aureus subsp. aureus ATCC 25923 16S-23S intergenic spacer sequence (U39769) SEQ ID NO 5

CTAAGGATATATTCGGAACATCTCTTCAGAAGATGCGGAATAACGTGACATATTGTATTCAGTTTGAATGTTT
ATTTAACATTCAAAAAATGGGCCTATAGCTCAGCTGGTTAGAGCGCACGCCTGATAAGCGTGAGGTCGGTGTTC
GAGTCCACTTAGGCCCACCATTATTGTACATTGAAAACTAGATAAGTAAGTAAAATATAGATTTTACCAAGCAA
AACCGAGTGAATAAAGAGTTTAAATAAGCTTGAATTCATAAGAAATAATCGCTAGTGTTCGAAAGAACACTCAC
AAGATTAATAACGTGTTTAAATCTTTTTATAAAATAAACGTTAGCAGACAATGAGTAAATTATTTAAAGCA
GAGTTTACTTATGTAAATGAGTATTAAAATAATGAAAACGAAGCCGTATGTTAACGTTTGACTTATAAAAATGG
TGGAAACATA

Staphylococcus chromogenes ATCC 43764 16S-23S intergenic spacer sequence (U39770) SEQ ID NO 6

CTAAGGATAATATACGGAATATCGCTTTTAAGCGATAAGGAATAACGGAGACATATTGTATTCAGTTTGAATGC
TCATTTCGAGGCATTCAACATTGTACATTGAAAACTAGATAAGTAAGTATAGATTTACCAAGCAAAACCGAGT
GACAAGCGAAAAGCTTGAAACAAAATTATCGCTAGTCGTCGACAGACSACTCACAATAATTAATAACTGGTGGA
TGTTGGTTATTGTTTAATTCGAAAGCCGAATGTAAACGATTGCCAAAACATCAAAA

Fig. 2D

Staphylococcus epidermidis ATCC 12228 16S-23S intergenic spacer sequence (U39771) SEQ ID NO 7

CTAAGGATATATTCGGAACATCTTCTACGAAGATGAGGGATAACGTGACATATTGTATTCAGTTTGAATGTTTA
TTAACATTCTTTGTACATTGAAAACTAGATAAGTAAGATTTTACCAAGCAAAACCGAGTGAATAGAGTTTT
AAATAAGCTTGAATTCATAAATAATCGCCTAGTGTTCGAAAGAACACTCACAAGATTAATAACTAGTTTTAGCTA
TTTATTTTTAATAACAATTCAAAATATGGTGGAAACATA

Staphylococcus hyicus KNS 264/92 16S-23S intergenic spacer sequence (U39772) SEQ ID NO 8

CTAAGGATAATATACGGAATATGCCCTTAGGCATACGGAATAACGAAGACATATTGTATTCAGTTTGAATGCTC
ATTTGAGGATTCAACATTGTACATTGAAAACTAGATAAGTAAGTATAGATTTTACCAAGCAAAACCGAGTGACA
AGCGAAAAGCTTGAAACAAAAAATTATCGCTAGTCGTCGACAGCGACTCACAATAATTAATAACTGGTGGATGTT
GGTTAATGTTTACTTCGGATGACAGATGTTTGAAAACGTTTGTCAGTCTATGAATCGCAAACAAGAGCGAAGGC
CGTTACTTCCGTAAGCAACTGAGTGATTTGTGCCGCGATGAAGCCGAATGCAAAACGATTGCCAAAACATCATAAA

Fig. 2E

Staphylococcus simulans ATCC 11631 16S-23S intergenic spacer sequence
(U39814) SEQ ID NO 9

(16S)spacer
(*CTTT*)CTAAGGATATATATTCGGAACAGTTTCGCAGGAAACTGAAACGTGACATATTGTATTCAGTTT
TGAATGTTTATTGAAACATTCAACGTGAGATGGGCCTATAGCTCAGCTGGTTAGAGCCGACGCCCTGATAAGCGT
GAGGTCGGTGGTTCGAGTCCACTTAGGCCCCACCATTTGATTTTTTGTACATTGAAAACTAGATAAGTAAGTAAA
AAATAGATTTACCAAGCAAAACCGAGTGAATTAGAGTTTAAAGCTTTATTCATTTAAATGAATCGCTAGTAA
TCAATTGCCGACGGCAAACGATTACTCACAATATTAATAAC Staphylococcus simulans ATCC 11631 16S-23S intergenic spacer sequence
(U39813) SEQ ID NO 10

(16S)spacer
(*CTTT*)CTAAGGATATATATTCGGAACAGTTTCGCAGGAAACNGGAATAACGTGACATATTGTATTCAGTT
TTGAATGTTTATTGAAACATTCAAAGATTGTACATTGAAAACTAGATAAGTAAGTAAAAAATAGATTTACCAA
GCAAAACCGAGTGAATTAGAGTTTAAAGCTTTATTCATTTAAATGAATCGCTAGTAATCAATTGCCGACGGCA
AACGATTACTCACAATATTAATAAC

Fig. 2F

Staphylococcus xylosus ATCC 12162 16S-23S intergenic spacer sequence
(U39773) SEQ ID NO 11

CTAAGGATATATTCGGAACATCTTCTTTAGAAGATGACAGAGGAATAACATTGACATATTGTATTCAGTTTTGAA
TGCTCATTGGAGTATTCAGTGCATAATTTGTACATTGAAAACTAGATAAGTAAGATAAATATATAGATTTACCA
AGAAAAACCGAGTGAATTAGAGTTTAAATAAGCTTGAATTCAAAAGAAATAATCGCTAGTGTTCGAAAGAACA
CTCACAGATTAATAACATTTTGGGTTTTTAACCGACTTCGTCGTGTTAAAAGTCAAAAAA

DNA-SEQUENCE-BASED DIAGNOSIS OF MASTITIS FROM A MILK SAMPLE

TECHNICAL FIELD OF THE INVENTION

The invention relates to a method for diagnosing mastitis by measuring the presence of specific DNA sequences in a milk sample. The invention further relates to a test kit and specific oligonucleotides for use in the method.

DESCRIPTION OF RELATED ART

Mastitis can be defined as an inflammation of the mammary gland. Mastitis is a disease the object of which can be a female of any mammalian species including man. From the economical point of view mastitis is the most important disease of dairy heifers and cows. In most cases mastitis is a result of colonization of the mammary gland by pathogenic bacteria (infection mastitis). In addition, physical injuries or local mechanical or chemical stresses in udder organs are able to trigger a local inflammation cascade without the involvement of any primary bacterial infection. Accordingly, these cases are also considered as mastitis, more precisely sterile mastitis.

The inflammatory state is associated with varying degrees of pathological damage to the mammary epithelium, resulting in subclinical or clinical mastitis. Clinical mastitis is often an acute inflammation, but inflammatory reactions in subclinical mastitis are often so mild that this state could easily remain unrecognized and without medical care. Most cases of subclinical mastitis represent a chronic subclinical form. Many recent surveys on the prevalence of dairy cow mastitis in western countries indicate that 30–50% of dairy cows suffer from mastitis, in most cases subclinical mastitis. Consequently, bovine mastitis causes vast economical losses to dairy farmers worldwide through reduced milk production, medical expenses and slaughter of chronic cases.

A mastitis diagnosis should be based on both an infection study and a study on the state of inflammation. The methods for detecting mastitis are classified as direct and indirect ones. Bacteriological isolation and examination is a test, which directly shows whether the milk studied is infected or not. This bacteriological approach relies on the assumption that the mammary gland is normally aseptic and the appearance of bacteria indicates infection mastitis. Because inflammation is a complex and multifactoral process, there are various tests, including both direct and indirect ones, for measuring inflammation within the mammary gland. Mastitis is known to cause many biochemical and biophysical changes in the composition of milk. These changes arise as a consequence of microbial invasion or non-microbial factors followed by counter-reactions of the body to these stimuli. The changes include active mobilisation of leucocytes (representing somatic cells together with epithelium cells) from the blood into the milk gland, passive diffusion of blood and alveoli epithelium cell components like proteins and ions, caused by local cell damage and tissue injury, following an alternation in the permeability of microcirculatory vessels.

The most commonly used marker for inflammation is somatic cell counting (SCC), which can be performed directly with a particle counter or a light microscope or indirectly with tests estimating the amount of SCC by parameters like milk viscosity after detergent treatment in the California Mastitis Test (CMT), the most common cowside screening test for inflammation.

In most cases mastitis is caused by infection of certain Staphylococcus or Streptococcus bacteria. As regards bovine mastitis among staphylococcal species S. aureus and certain coagulase negative species (CNS), especially *S. hyicus, S. chromogenes* (also classified as *S. hyicus* ssp. chromogenes), *S. simulans, S. epidermidis*, and *S. xylosus* are the most common ones. Among streptococci the important bovine mastitis pathogens include *Str. agalactiae, Str. dysgalactiae, Str. uberis* and *Str. bovis* species. Only a few percent of infection mastitis is caused by some other bacteria like *Escherichia coli* and Actinomyces or by eukaryotic microbes, yeasts and molds. *S. aureus* is the most common pathogen causing clinical mastitis. CNS have been considered as minor pathogens because they are inhabitants of the skin and mucous membranes. CNS are, however, important, because they are commonly involved in subclinical mastitis and also in clinical mastitis among heifers. Presently streptococcal mastitis pathogens are still important especially in cases of chronic mastitis and mastitis primarily caused by teat canal trauma.

The contribution of different streptococcal and staphylococcal species on bovine mastitis seems to depend on the habits and practise of both animal husbandry and veterinarian therapy. Especially the transition from hand milking to milking machines and the wide use of broadspectrum antibiotics have had strong influence on the species spectrum of mastitis pathogens. Streptococcal species, especially *Str. agalactiae*, were the most frequent mastitis pathogens until the use of milking machines spread in the 1950's and 1960's, when they were replaced mainly by *S. aureus*. In the 1970's the importance of CNS as bovine mastitis pathogens was still marginal. During the last twenty years the CNS have increased their proportions with a simultaneous decrease in the proportion of *S. aureus* as mastitis pathogens. This change coincides with the widespread use of broad specturm antibiotics like penicillin-G that is still the most important antibiotic drug in mastitis therapy.

One serious consequence of the use of antibiotics has been the emergence of antibiotic-resistant strains. Presently this also holds true for bovine mastitis pathogens. Genes encoding antibiotic resistance are able to recombine by transposons and to transfer further between bacterial species by conjugation, transformation or transduction. Especially the CNS have been found to receive and further transfer these kinds of antibiotic resistance genetic determinants more easily than *S. aureus* (Owens & Watts, J. Dairy Sci. 71 (1988) 1934–1939; Muhammad et al., Amer. J. Vet. Res. 54 (1993) 1432–1440). Consequently, differences in susceptibilities between *S. aureus* and CNS to various antibiotics widely used in bovine mastitis therapy may have caused a selective advantage to CNS over *S. aureus* and increased the proportion of CNS as mastitis pathogens.

About one third of *S. aureus* strains isolated from bovine mastitis have proved to be resistant to penicillin-G. This proportion is somewhat smaller among CNS species (Myllys, J. Dairy Res. 62 (1995) 51–60). The level of penicillin resistance encoded by β-lactamase gene blaZ is dependent on the levels of transcriptional and translational expression of this gene. The tests used for penicillin resistance screening are not always sensitive enough to detect strains expressing the blaZ gene weakly. This is problematic, because this kind of false negative test result may lead to false penicillin therapy and to positive selection of blaZ gene among mastitis pathogens.

Presently, good laboratory practice of mastitis diagnosis includes both an inflammation study and a bacteriological study of the milk sample. As a rapid and simple test for measuring the degree of inflammation, the CMT is sensitive enough in detecting clinical mastitis, but not always subclinical mastitis. Even the SCC as a direct test is not sensitive enough for the diagnosis of subclinical mastitis due to great physiological and individual variations in the somatic cell level of milk. Repeated testing and interquarter comparison of SCC levels between the four quarters of the udder shall improve the probability of detecting the positive subclinical cases, for it is statistically rare that all four quarters of the udder are inflamed simultaneously and to the same degree. A bacteriological study should include both an isolation trial of the mastitis pathogen and furthermore, if a pathogen is detected, antimicrobial susceptibility testing for a proper antibiotic treatment. As a test, the bacteriological cultivation of the milk sample is slow, because bacterial colonies can be analyzed at the earliest after one day of incubation, but typically after two days. It is possible to perform antimicrobial susceptibility testing only after the isolation of the bacterium. If the traditional Bauer-Kirby disk diffusion method (Bauer et al., Am. J. Clin. Pathol. 45 (1966) 493–496) is used, it will take about one day. Presently certain biochemical and enzymatic tests are more rapid giving results in a few hours. This kind of bacteriological study of a milk sample still takes altogether at least one day, but typically two days, before all the necessary data required for a correct mastitis diagnosis and therapy by a veterinarian is available. A delay of even one day in the start of the care of mastitis will cause considerable economical losses to the farmers. Consequently, a more rapid mastitis diagnosis is highly desirable among both veterinarians and farmers.

SUMMARY OF THE INVENTION

Accordingly it is an object of the present invention to shorten the time needed for a proper mastitis diagnosis, i.e. a diagnosis indicating the presence of inflammation, infection and drug resistance. Another object of the invention is to enable identification of a possible infection agent. These and other objects are accomplished by an alternative approach to performing a mastitis diagnosis which is wholly based on measuring the presence of specific DNA sequences in a milk sample.

The present invention therefore provides a method for diagnosing mastitis comprising the steps of determining the presence of the following DNA sequences in a milk sample: a DNA sequence specific for somatic cells for indicating inflammation; a DNA sequence specific for a mastitis pathogen for indicating infection; and a DNA sequence specific for an antibiotic-resistance-encoding gene of a pathogen for assisting a proper drug therapy.

Another object of the present invention is to provide a test kit and oligonucleotides useful in the DNA-sequence-based method for diagnosing mastitis. The present invention thus provides a test kit for diagnosing mastitis from a milk sample comprising at least the following oligonucleotides: an oligonucleotide which specifically hybridizes with a DNA sequence specific for somatic cells; an oligonucleotide which specifically hybridizes with a DNA sequence specific for a mastitis pathogen; and an oligonucleotide which specifically hybridizes with a DNA sequence specific for an antibiotic-resistance-encoding gene. The present invention further provides oligonucleotides for use in a method for diagnosing mastitis from a milk sample, said oligonucleotide specifically hybridizing with a mastitis-pathogen-specific DNA sequence substantially from the 16S–23S rRNA spacer region of the pathogen.

BRIEF DESCRIPTION OF THE DRAWINGS

FIGS. 2A–2F presents the 16S–23S rRNA intergenic spacer sequences of the ten most important bovine mastitis bacterial species. (GenBank accession numbers are given in brackets, selected species-specific subsequences are in bold print and flanking 16S and 23S rRNA gene sequences are in brackets.)

DETAILED DESCRIPTION OF THE INVENTION

Figure 1:
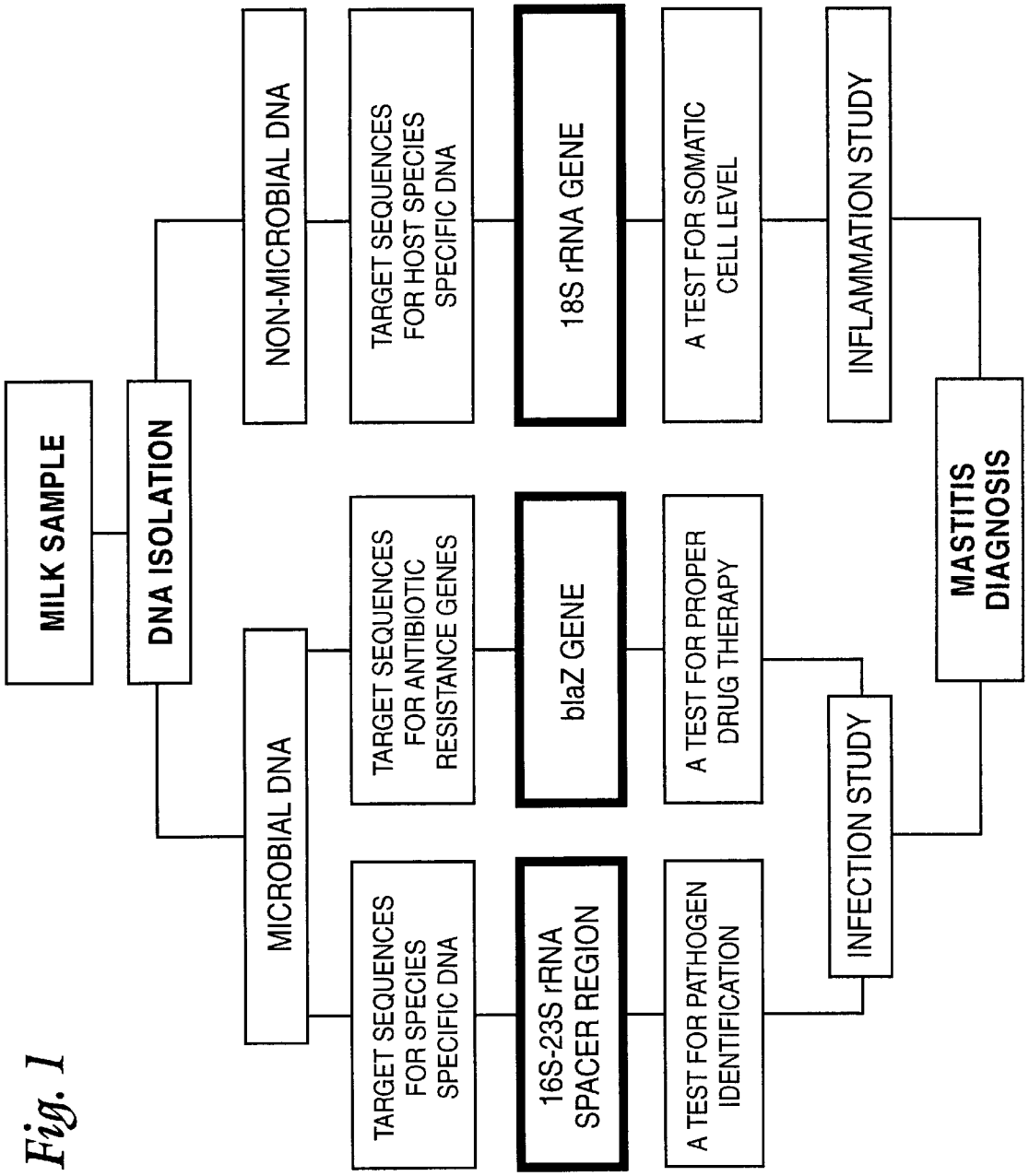
FIG. 1 is a flow chart illustrating the principle of the invention.

The present invention makes it possible to perform a proper mastitis diagnosis in only a few hours or even in a shorter time. Despite this short time the invention makes it possible to identify a pathogen even at the species level and to test for antibiotic resistance. The principle of the invention is illustrated in the flow chart of FIG. 1. DNA is isolated from a milk sample from a female mammalian suspected to suffer from mastitis. The mammalian can be of any species, including man. Preferably it is a dairy heifer or a cow. For inflammation study the presence of a host-specific target sequence is determined, and for infection study the presence of a target sequence specific for a mastitis pathogen and a target sequence specific for antibiotic resistance are determined. This kind of molecular genetic tests do not require any bacterial cultivation and isolation, but can be performed directly on the isolated DNA. Preferably the host-specific target sequence is from the conserved region of a bovine 18S rRNA gene and preferably the pathogen-specific target sequence is substantially from the 16S–23S rRNA spacer region of a Streptococcus or Staphylococcus mastitis bacterium, it is especially from any of SEQ ID NO 1–11 or from the complementary strands thereof. The target sequence specific for an antibiotic-resistance-encoding gene is preferably from the blaZ gene encoding resistance to β-lactam antibiotics.

The present invention is very useful for detecting bacterial mastitis pathogens especially from the genus Streptococcus or Staphylococcus, in which case it is practical to first identify a genus-specific sequence and thereafter, if desired, the appropriate species-specific sequence. Preferred embodiments of the invention are also set forth in the dependent claims.

The presence of the target sequences can be determined in any conventional way e.g. by hybridization or preferably by polymerase chain reaction (PCR) as previously described e.g. in Ehrmann et al., FEMS Microbiol. Lett. 117 (1994) 143–150 and Barry et al., PCR Methods and Applications 1 (1991) 51–56, respectively. For hybridization purposes, the isolated DNA is first denaturated and then reacted with e.g. a labeled complementary probe under conditions enabling hybridizaton, whereafter the amount of hybrid-bound probe is measured. In PCR, a primer pair is used which recognizes complementary strands of the DNA segment to be enzymatically amplified. The amplified DNA segment (usually about 0.2–2 kb) can then be detected e.g. by gel electrophoresis. Oligonucleotides of about 15 to 25 nucleotides are preferably used as hybridizing probes or primer pairs for PCR. "Oligonucleotide" as used herein means a relatively short preferably synthetic nucleotide molecule usually comprising less than 100 nucleotides.

Oligonucleotides "specifically hybridizing" means oligonucleotides which are complementary to the target sequence or which are sufficiently complementary to hybridize with said target sequence but not with interfering sequences. "Substantially" as used in connection with a DNA sequence substantially from the 16S–23S rRNA spacer region means that said sequence is mainly derived from the spacer region, although it may comprise further sequences e.g. from the flanking 16S rRNA and/or 23S rRNA genes as shown (in brackets) in FIG. 2. "Target sequence" means the sequence to which the oligonucleotide probe or primer hybridizes.

Identification of a mastitis pathogen is required for infection study. More than 99% of the mastitis pathogens are bacteria. A successful strategy in nucleic-acidsequence-based identification of bacterial species has shown to be the application of phylogenetic differences among sequences of ribosomal RNA operons (rrn) present in every prokaryotic chromosome (Barry et al., BioTechnology 8 (1990) 233–236). The 5S, 16S and 23S RNA genes of the rrn operons contain both conserved and variable regions. These conserved regions allow the design of universal oligonucleotide primers with which the amplification of rrn DNA segments from any bacterial DNA is possible by PCR. Nucleotide sequences of these amplified DNA segments can be determined and species-specific oligonucleotides can be designed based on the observed differences in sequences among various bacterial species. So far most species-specific oligonucleotides have been derived from variable regions of 16S and 23S rRNA genes. However, there are situations where very little variation is observed within said genes, in which case species-specific sequences derived from the spacer (intergenic) region between the 16S and 23S rRNA genes offer a considerable alternative. In fact, the intergenic regions have been found to present higher sequence variability than the variable regions of rRNA genes (Barry et al., PCR Methods and Applications 1 (1991) 51–56; EP-A1-0452596).

In order to find diagnostically useful species- or genus-specific nucleotide sequences for the identification of mastitis bacteria, nucleotide sequence data on rrn operons is required. However, it turned out that this kind of published sequence data on relevant mastitis bacteria is very limited (until Nov '95 only sequences of 16S–23S rRNA gene of *S. aureus* (Gürtler & Barrie, Microbiology 141 (1995) 1255–1265) and *Str. agalactiae* (GenBank Acc. n:o L31412) have been described in various sequence data banks available). Consequently, the 16S–23S rRNA gene spacer sequences of the ten most important Staphylococcus and Streptococcus species causing bovine mastitis were determined and are presented in FIG. 2 (SEQ ID NO 1–11). The nucleotide sequences of the conserved and consequently general oligonucleotides used as primer pairs for the PCR amplifications of these 16S–23S rRNA gene segments are presented in Table I SEQ ID NO 36/37 and 38/39.

The 16S-23S rRNA spacer sequences from the ten mastitis bacteria species were further analyzed in order to design species- and genus-specific oligonucleotides for each case. This approach turned out to be successful and the species-specific oligonucleotide primer pairs for each of the ten mastitis bacteria species considered in this study could be designed as shown in Table II (SEQ ID NO 12–31). These sequences are derived from SEQ ID NO 1–11 or their complementary strands, i.e. they are either subsequences or inverted complementary subsequences of SEQ ID NO 1–11. The regions they derive from are in bold print in FIG. 2. Furthermore, it was possible to design Streptococcus and Staphylococcus genus-specific primer pairs and they are also included in Table II (SEQ ID NO 32/33 and 34/35). Species and genus specificities of each of the twelve primer pairs of Table II were tested by PCR and the results are summarized in Table III. As shown with each primer pair, a PCR product was obtained species- and genus-specifically as designed and expected without any false positive or negative PCR amplifications.

For the infection study of mastitis, it is desirable to link mastitis pathogen identification with antimicrobial resistance screening. In the present invention, the simultaneous analysis of bacterial species and the screening of (a) desired resistance gene(s) from the same DNA sample is possible by PCR with specific primer pairs. In practise, the simultaneous screening of one or a few genetic resistance determinants is reasonable. The most widely used antimicrobial drug for mastitis is penicillin and its derivatives like ampicillin, which are members of the βlactam antibiotic group. Accordingly the screening of the gene blaZ encoding β-lactamase is one of the priority choices in mastitis diagnosis. As demonstrated in Table IV, the general primer pair BLAZ I/BLAZ II (SEQ ID NO 42/43, see Table I) for blaZ gene is a proper choice to screen penicillin-resistant strains among mastitis bacterial strains tested. In principle screening for any genotypic resistance determinant can be performed from the DNA sample if sequence data required for oligonucleotides as a probe or primers is available. Bacteriological study of a mastitis milk sample by PCR with specific primer pairs can be performed directly and correctly after the DNA has been isolated from the milk sample as demonstrated in Table V. For bacterial DNA isolation, a relatively simple and rapid procedure has been described in Example 6.

The level of SCC in a milk sample can be estimated for inflammation study on the basis of the amount of eukaryotic DNA in the sample (FI patent 90788). This strategy requires a method which distinguishes eukaryotic DNA from prokaryotic and viral DNAs. This requires the use of techniques by which eukaryotic DNA can be identified based on the unique genetic information that is present in eukaryotic DNA, but absent in prokaryotic or viral DNAs. For example histone genes, ribosomal RNA (rRNA) genes and their most conserved regions represent this kind of ubiquitous and conserved eukaryotic DNA markers. Two oligonucleotide sequences of this kind, P1b/P2b (SEQ ID NO 40/41), derived from 18S rRNA gene sequences (FI patent 90788) are shown in Table I. These two oligonucleotides specifically hybridize with the conserved regions of eukaryotic 18S rRNA genes and accordingly can be used as probes for these genes or alternatively as a primer pair for the amplification of these gene regions by polymerase chain reaction (PCR). The amplified eukaryotic 18S rRNA gene fragment can be sequenced. There are sequence differences between the 18S rRNA genes of different eukaryotic species like human (*Homo sapiens*), bovine (*Bos taurus*) and so on (FI patent 90788). If required, these sequence differences can be applied to the design of eukaryote species-specific oligonucleotides. In practise, this is required only occasionally for inflammation study. The general oligonucleotides P1b/P2b (SEQ ID NO 40/41) described in Table I are specific enough to estimate SCC levels in mastitis milk samples as demonstrated in Table VI (example 7). Only in those rare cases (frequency of less than 1%) where a eukaryotic microbe that is a yeast or a mold causes mastitis, specific oligonucleotides derived from eukaryotic microbe 18S rRNA gene sequences could be applicable.

In summary, for the purpose of a mastitis diagnosis both the infection study and the inflammation study can be performed by PCR with specific primer pairs simultaneously after DNA from the mastitis milk sample has been isolated using relatively simple and rapid procedures as shown in examples 6 and 7. The time required for isolating DNA from a milk sample for PCR reactions was less than 130 min. The DNA amplification step took about 110 min with a conventional PCR device (example 2), but only 20 min with an ATC-type PCR device (example 3). An analysis of PCR products with agarose gel electrophoresis (with 150 V voltage in 1.5% agarose in 1x TBE buffer) in the presence of ethidium bromide could be performed in 15 min. It is also possible to use alternative systems to measure (semi) quantitatively the amounts of ds-DNA after PCR reactions e.g. fluorometrically or immunologically using ds-DNA specific stain or antibodies, respectively. Altogether, the time required for a DNA-sequence-based mastitis diagnosis was less than about 4 h or 3 h when a conventional or ATC-type PCR device, respectively, was operated for PCR. Because of the bacteriological cultivation of a milk sample, a conventional mastitis diagnosis requires at least 24 hours and typically double the time. Accordingly, the DNA-sequence-based mastitis diagnosis described here will drastically increase the speed of mastitis diagnosis to at least eight-fold without any loss of necessary information required for a correct diagnosis.

It should be understood that the detailed description above and the following specific examples, while indicating preferred embodiments of the invention, are given by way of illustration only, since various changes and modifications within the spirit and scope of the invention will become apparent to those skilled in the art and are intended to be included within the scope of the claims.

EXAMPLE 1

Extraction of Bacterial DNA for Sequence Determination

Each mastitis bacterial strain included in this study was grown overnight in a proper culture medium (Tryptic Soy Broth). Bacterial cells were collected by centrifugation (14,000 g/5 min) at 4° C. and washed twice with 10 mM Tris-HCl-buffer, pH 7.0. The washed bacterial cells were suspended in 10 mM Tris-HCl-buffer, pH 7.0, containing 12% (w/v) PEG 6000 and 10 mg/ml lysozyme (Sigma Chemical Co, St. Louis, U.S.A.), and the suspension was incubated for 30 min at 37° C. The cells were collected by centrifugation (10,000 g/15 min) at 4° C., lysis buffer (10 mM EDTA-20mM Tris-HCl-buffer, pH 7.0, containing 3% (w/v) SDS) was added to the cell pellet, and the cell suspension was incubated for 30 min at room temperature. The clarified cell solution was extracted twice with a phenol-chloroform-isoamylalcohol(25:24:1) mixture, after which the bacterial DNA was precipitated from the water phase with 200 mM NaCl and 50% (v/v) isopropanol. The DNA was collected by centricentrifugation and washed with 70% EtOH, dried and resuspended in proper volume of TE-buffer (10 mM Tris-HC1, 1 mM EDTA, pH 8.0).

EXAMPLE 2

Amplification and Sequencing of 16S–23S rRNA Intergenic Regions

The 16S–23S spacer regions were amplified from the bacterial DNA by PCR (Saiki et al., Science 239 (1988) 487–491). The primer sequences used for amplifying the DNA segment represented conserved regions at the 3'-end of the 16S rRNA-gene and at the 5'-end of the 23S rRNA-gene. The oligonucleotide sequences of the primer pairs 16-1D/23-1D (SEQ ID NO 36/37) and 16-1A/23-1B (SEQ ID NO 38/39) used for staphylococcal and streptococcal species, respectively, are shown in Table I. The PCR reactions were carried out in DNA Thermal Cycler 480 (Perkin Elmer, Norwalk, U.S.A.) using DynaZyme DNA Polymerase kit (Finnzymes, Espoo, Finland).

A typical PCR reaction mixture contained sterile distilled water, reaction buffer (10 mM Tris-HCl, pH 8.8, 1.5 mM $MgCl_2$, 50 mM KCl, 0.1% Triton), 200 $\mu$M dNTP, 0.6 $\mu$M of each primer, 5 ng of bacterial DNA and 1.2U (0.6 $\mu$l) DynaZyme DNA polymerase solution/100 $\mu$l of reaction mixture. The reactions were overlayed with mineral oil to prevent evaporation of the mixture.

The parameters of the PCR reaction cycle were: 30 sec at 95° C. (denaturation), 30 sec at 55° C. (annealing) and 30 sec at 72° C. (extention). The cycle number was 30. Before the first cycle the sample tubes were incubated for 2 min at 95° C. The PCR amplification was finished with 10 min extention at 72° C. followed by a cooling step down to 4° C. The total time required for the PCR amplifications of the DNA samples was about 110 minutes. The PCR reaction products (expected size about 500–700 bp) were analyzed with agarose gel electrophoresis. The excess primers and nucleotides were removed from the products with QIAquick PCR-purification kit (QIAGEN, Hilden, Germany).

The 16S–23S rRNA intergenic spacers were sequenced directly from the PCR products by cycle sequencing using a CircumVent Thermal Cycle Dideoxy DNA-sequencing kit (New England Biolabs. Inc., Beverly, U.S.A.). In sequencing reactions 3 $\mu$l (50–100 ng) of the obtained DNA solution was used and the reactions were carried out in the PCR thermal cycler. The parameters of the sequencing reaction cycle were: 40 sec at 95° C., 30 sec at 55° C. and 2 min at 72° C. The cycle number was 15. The sequencing samples were analyzed with polyacrylamide gel electrophoresis.

In the cases where the PCR product consisted of primary and secondary products, the primary product was excised from the agarose gel and purified with QIAquick gel extraction kit (QIAGEN, Hilden, Germany). This DNA was used as a template in a second round of PCR, after which the PCR products were purified as above. PCR products of some samples (*S. aureus, S. simulans, S. epidermidis, S. hyicus* and *S. xylosus*) were cloned using a TA Cloning Kit (Invitrogen, San Diego, U.S.A.) and sequenced using a Sequenase Version 2.0 DNA-sequencing kit (United States Biochemical, Cleveland, U.S.A.) because a direct sequencing method failed to give enough readable sequence.

EXAMPLE 3

Design of Species- and Genus-Specific Oligonucleotides for Identification of Mastitis Bacterial Species The species- and genus-specific sequence regions were analyzed from the 16S and 23S rRNA intergenic nucleotide sequences of each of the ten mastitis bacterial species studied, and they are presented in FIG. 2 (SEQ ID NO 1–11). In the case of *S. simulans*, two sequence variants were determined. Based on the sequence analysis, oligonucleotides suitable for use as species- and genus-specific primers were designed from both ends of the spacer (near to or including a few nucleotides from the 16S rRNA and 23S rRNA genes) and they are presented in Table II (SEQ ID NO 12–35). The oligonucleotides were synthesized by the oligonucleotide synthesis service unit at the Department of Biochemistry, University of Oulu, Oulu, Finland by commercially available equipment according to the manufacturer's instructions.

PCR reactions were carried out as described in example 2, but instead of general primers, one of the species- or genus-specific primer pairs described in Table II was used. In addition, the $MgCl_2$-concentration was 3.0 mM for primer pairs Dy I & Dy II, Ep I & Ep II and Str I & Str II, and 4.0 mM for primer pairs Ag I & Ag II and Bo I & Bo II. The PCR products (expected size about 250–350 bp) were analyzed with agarose gel electrophoresis. Table III summarizes reactions with each primer pair and each bacterial DNA tested.

EXAMPLE 4

Rapid PCR with Specific Primer Pairs

PCR reactions with specific primer pairs presented in Table II were also carried out in a RapidCycler thermal cycler (Idaho Technology, Idaho Falls, U.S.A.). With this type of cycler (ATC, Air Thermal Cycler) it is possible to significantly reduce the time required for DNA amplifications. PCR reactions contained a reaction buffer (67 mM Tris-HCl, pH 8.8, 16 mM $(NH_4)_2SO_4$; 0.01% Tween-20), 3 mM $MgCl_2$ (except for 4 mM for the primer pair Hy I/Hy II and 5 mM for BlaZ I/BlaZ II), 200 µM dNTP, 0.25 µg/µl of BSA, sterile water, 5 ng of bacterial DNA and 0.6 µAM of each primer. The reaction volume was 10 µl and glass capillaries were used instead of microcentrifuge tubes.

The parameters of the rapid PCR cycle were: 0 sec at 94° C., 0 sec at 55° C. and 15 sec at 72° C., the cycle number being 30. The program was preceded by a denaturation step for 15 sec at 94° C. PCR products were analyzed with agarose gel electrophoresis as in example 2. The PCR products obtained with the rapid PCR were similar to the PCR products obtained with the conventional PCR. In summary, with the rapid PCR the amplifications were completed in 20 min, which was about six times faster than the completion of the amplifications with the conventional PCR (about 110 min), as shown in examples 2 and 3.

EXAMPLE 5

Determination of Bacterial Resistance to β-lactam Antibiotics

The presence of β-lactamase gene (blaZ) in bacterial DNA was determined by PCR amplification with specific primers, BLAZI and BLATZII (SEQ ID NO 42/43). The primers applied for amplifying the blaZ gene region were based on a comparison of available GenBank blaZ gene sequences from *Bacillus cereus* and *Staphylococcus aureus* (for sequences and references see Table I). The PCR reactions and the analysis of the PCR products (expected size about 260 bp) were carried out as described in example 2. For comparison, the antibiotic resistance was tested also by analyzing the growth of bacteria in Bacto tryptic soy broth (Difco) medium containing 25 µg/ml of ampicillin (Boehringer Mannheim). Bacteria were incubated overnight at 37° C. with constant agitation. The results from these experiments are summarized in Table IV. As shown, the results from the DNA-sequence-based detection of blaZ gene by PCR are in fully agreement with the results from the conventional cultivation tests. The resistance was previously determined only for *S. simulans* ATCC 11631, which is a penicillin-resistant genotype (penR, for ref. see ATCC Catalogue of Bacteria and Bacteriophages, 18th edition, 1992). It was used as a positive control.

EXAMPLE 6

Infection Study from Mastitis Milk Samples by PCR

Twenty µl of a milk sample in a 1.5 ml Eppendorf tube was mixed with 200 µl of phosphate-buffered saline (PBS), and further centrifuged for 5 min at 12,000 g. The supernatant was removed by pipetting. The remaining visible pellet containing cells was suspended into STE-sucrose buffer (100 mM NaCl, 10 mM Tris-HCl pH 8.0, 1 mM EDTA, 20% sucrose) containing mutanolysin 500 units/ml (Sigma). The suspension was incubated at 37° C. for 60 min, and further centrifuged for 5 min at 12,000 g. The supernatant was discarded and the remaining pellet was suspended into 20 µl of lysis buffer (50 mM KCl, 10 mM Tris-HCl pH 8.0, 1% Tween 20, 1 mg/ml proteinase K). The suspension was incubated for 60 min at 60° C. Finally, the suspension was boiled in a waterbath for 10 min. PCR reactions (15 µl in volume) were carried out as described in example 2 using bacterial genus- or species-specific or eubacterial primer pairs, but instead of purified DNA, 1 µl of lysed cell suspension obtained above and cycle number 40 instead of 30 were used. The PCR products were analyzed as described in example 2 (expected size about 250–350 bp when a species- or genus-specific primer pair was used or about 500–700 bp when a eubacterial primer pair was used). For comparison, conventional bacteriological study was done for the same mastitis milk samples. The test strategy and the results are shown in Table V demonstrating that the results from the bacteriological study of mastitis by PCR with specific primer pairs were fully in agreement with the results from the conventional bacteriological study. In fact, in two cases the results obtained from the DNA-sequence-based study were more precise than those obtained from the bacteriological diagnosis.

EXAMPLE 7

Inflammation Study from Mastitis Milk

For estimation of the level of somatic cells in a milk sample, PCR with the primer pair derived from 18S rRNA gene sequences (Table I) was done. One µl of milk was added to 200 µl of 40 mM NaOH in a 1.5 ml Eppendorf tube in order to reach a proper dilution. The diluted sample was boiled for 10 min in a waterbath to lyse the somatic cells. The PCR reaction (15 µl in volume) was carried out as described in example 2, using the primer pair P1b/P2b (SEQ ID NO 40/41), but instead of purified DNA, 1 µl of lysed cell mixture obtained above was used. The PCR products (expected size about 170 bp) were analyzed with agarose gel electrophoresis and the amount of DNA in the PCR products was quantitated by a densitometer. For comparison, the same milk samples were also analyzed by two conventional SCC tests, that is the CMT (California Mastitis Test) and Fossomatic cell counting. These tests were performed by a clinical laboratory. The results from these comparative studies have been summarized in Table VI. These results demonstrate that the DNA-based SCC determination is as informative as the conventional SCC tests.

TABLE I

Sequences of oligonucleotides used as general primer pairs for molecular genetic mastitis diagnosis

| Target gene | Oligonucleotide | SEQ ID NO | Sequence | Direction | Reference |
|---|---|---|---|---|---|
| Eukaryotic 18S rRNA gene | P1b | 40 | AGGAATTCCCAGTAAGTGC | > > > > | a |
| Eukaryotic 18S rRNA gene | P2b | 41 | AGATAGTCAAGTTCGACCG | < < < < | a |
| Eubacterial 16S rRNA gene | 16-1D | 36 | GGTGAATACGTTCCCGGG | > > > > | b |
| Eubacterial 23S rRNA gene | 23-1D | 37 | CTTACAGCTCCCCAAAGCAT | < < < < | b |
| Staphylococcal 16S rANA gene | 16-1D | 36 | GGTGAATACGTTCCCGGG | > > > > | b |
| Staphylococcal 23S rRNA gene | 23-1D | 37 | CTTACAGCTCCCCAAAGCAT | < < < < | b |
| Streptococcal 16S rRNA gene | 16-1A | 38 | GTCGGAATCGCTAGTAATCG | > > > > | b |
| Streptococcal 23S rRNA gene | 23-1B | 39 | GGGTTCCCCCATTCGGA | < < < < | b |

TABLE I-continued

Sequences of oligonucleotides used as general primer pairs for molecular genetic mastitis diagnosis

| Target gene | Oligonucleotide | SEQ ID NO | Sequence | Direction | Reference |
|---|---|---|---|---|---|
| Penicillin resistance gene blaZ | BlaZ I | 42 | GCTCATATTGGTGTTTATGC | > > > > | c |
| Penicillin resistance gene blaZ | BlaZ II | 43 | ATCACTATATGTCATTGAAGC | < < < < | c | a) FI-patent 90788
b) alignments of streptococcal and staphylococcal 16S and 23S rRNA gene sequences available in GenBank eg. X59028, X59030, X58317, Z22809, X59032, X68417, X68425, S60799
c) GenBank accession numbers M15195, M15526, Z04121, X16471, X52734

TABLE II

Streptococcus and Staphylococcus species- and genus-specific oligonucleotide sequences substantially from 16S–23S rRNA intergenic spacerregions suitable as primers and probes for molecular genetic mastitis diagnosis

| Genus/species | Oligo-nucleotide | SEQ ID NO | Sequence (5'→3') | Length (nt) | Direction (16S–23S) | Location (spacer) |
|---|---|---|---|---|---|---|
| Str. agalactiae | STRA-AgI | 12 | GGAAACCTGCCATTTGCG | 18 | > > > > | 16S-end |
|  | -AgII | 13 | TAACTTAACCTTATTAACCTAG | 22 | < < < < | 23S-end |
| Str. bovis | STRB-BoI | 14 | GGAAGCACGTTTGGGTATT | 19 | > > > > | 16S-end |
|  | -BoII | 15 | AACCTTATTTTGGTTCTGTTG | 21 | < < < < | 23S-end |
| Str. dysgalactiae | STRD-DyI | 16 | TGGAACACGTTAGGGTCG | 18 | > > > > | 16S-end |
|  | -DyII | 17 | CTTTTACTAGTATATCTTAACTA | 23 | < < < < | 23S-end |
| Str. uberis | STRU-UbI | 18 | TAAGGAACACGTTGGTTAAG | 20 | > > > > | 16S-end |
|  | -UbII | 19 | TCCAGTCCTTAGACCTTCT | 19 | < < < < | 23S-end |
| S. aureus | STAA-AuI | 20 | TCTTCAGAAGATGCGGAATA | 20 | > > > > | 16S-end |
|  | -AuII | 21 | TAAGTCAAACGTTAACATACG | 21 | < < < < | 23S-end |
| S. chromogenes | STAC-ChrI | 22 | ACGGAATATCGCTTTTAAGC | 20 | > > > > | 16S-end |
|  | -ChrII | 23 | CGTTTACATTCGGCTTTCG | 19 | < < < < | 23S-end |
| S. epidermis | STAE-EpI | 24 | TCTACAAGATGAGGGATA | 19 | > > > > | 16S-end |
|  | -EpII | 25 | TTTCCACCATATTTTGAATTGT | 22 | < < < < | 23S-end |
| S. hyicus | STAH-HyI | 26 | TACGGAATATCGCCTTAGG | 19 | > > > > | 16S-end |
|  | -HyII | 27 | AAAACATCTGTCATCCGAAG | 20 | < < < < | 23S-end |
| S. simulans | STAS-SiI | 28 | CTTTCTAAGGATATATTCGG | 20 | > > > > | 16S-end |
|  | -SiII | 29 | ATTGTGAGTAATCGTTTGCC | 20 | < < < < | 23S-end |
| S xylosus | STAX-XyI | 30 | TCTTTAGAAGATGACAGAGG | 20 | > > > > | 16S-end |
|  | -XyII | 31 | TGACTTTTAACACGACGAAG | 20 | < < < < | 23S-end |
| Streptococcus-genus | STR I | 32 | TGTTTAGTTTTGAGAGGTCTTG | 22 | > > > > | 16S-end |
|  | STR II | 33 | CGTGGAATTTGATATAGATATTC | 23 | < < < < | 23S-end |
| Staphylococcus-genus | STA | 34 | GGAATAACGTGACATATTGTA | 21 | > > > > | 16S-end |
|  | STA II | 35 | TTCACTCGGTTTTGCTTGG | 19 | < < < < | 23S-end |

(STRA = *Streptococcus agalactiae*, STRB = *Str. bovis*, STRD = *Str. dysgalactiae*, STRU = *Str. uberis*, STAA = *Staphylococcus aureus*, STAC = *S. chromogenes*, STAE = *S. epidermidis*, STAH = *S. hyicus*, STAT = *S. simulans*, STAX = *S. xylosus*, STR = Streptococcus sp., STA = Staphylococcus sp.

TABLE III

Species and genus specificities of the 12 primer pairs described in Table II as determined separately by PCR amplification of bacterial DNA from each of the ten mastitis Streptococcus or Staphylococcus species

| Bacterial species | PCR amplification with primer pair[a] | | | | | | | | | | | |
|---|---|---|---|---|---|---|---|---|---|---|---|---|
|  | STR | STA | STRA | STRB | STRD | STRU | STAA | STAC | STAE | STAH | STAS | STAX |
| *Str. agalactiae* | + | − | + | − | − | − | − | − | − | − | − | − |
| *Str bovis* | + | − | − | + | − | − | − | − | − | − | − | − |
| *Str. dysgalactiae* | + | − | − | − | + | − | − | − | − | − | − | − |
| *Str. uberis* | + | − | − | − | − | + | − | − | − | − | − | − |
| *S. aureus* | − | + | − | − | − | − | + | − | − | − | − | − |
| *S. chromogenes* | − | + | − | − | − | − | − | + | − | − | − | − |
| *S. epidermidis* | − | + | − | − | − | − | − | − | + | − | − | − |
| *S. hyicus* | − | + | − | − | − | − | − | − | − | + | − | − |
| *S. simulans* | − | + | − | − | − | − | − | − | − | − | + | − |
| *S. xylosus* | − | + | − | − | − | − | − | − | − | − | − | + |

[a]Primer pairs: STRA = Ag I & Ag II, STRB = Bo I & Bo II, STRD = Dy I & Dy II, STRU = Ub I & Ub II, STAA = Au I & Au II, STAC = Chr I & Chr II, STAE = Ep I & Ep II, STAH = Hy I & Hy II, STAS = Si I & Si II, STAX = Xy I & Xy II, STR = Str I & Str II and STA = Sta I & Sta II
+ = PCR product obtained
− = no PCR product

TABLE IV

Resistance of certain mastitis bacterial strains to β-lactam
antibiotics as determined by cultivation test and by PCR

| Bacterial strain | Observed sensitivity to ampicillin (25 μg/ml) in growth medium | Presence of blaZ gene determined by PCR |
|---|---|---|
| *Str. agalactiae* ATCC 27956 | S | − |
| *Str. bovis* ATCC 27960 | S | − |
| *Str. dysgalactiae* ATCC 27957 | S | − |
| *Str. uberis* ATCC 27958 | S | − |
| *S. aureus* ATCC 25923 | S | − |
| *S. chromogenes* ATCC 43764 | S | − |
| *S. epidermidis* ATCC 12228 | R | + |
| *S. hyicus* KNS 264/92 | S | − |
| *S. simulans* ATCC 11631 (penR) | R | + |
| *S. xylosus* ATCC 12162 | S | − |

S = sensitive (no growth),
R = resistant (growth),
− = no PCR product with BLAZI and BLAZII primers,
+ = PCR product obtained with BLAZI and BLAZII primers (table I).

TABLE V

Bacteriological study from mastitis milk samples as determined
by conventional bacteriological cultivation and examination
procedures and by PCR with specific primer pairs

| Sample No. | Microbiological study[a] | Primer pair used for PCR[b] | | | | | | | | | | | |
|---|---|---|---|---|---|---|---|---|---|---|---|---|---|
| | | EB[c] | STA | STAA | STAC | STAE | STAH | STAS | STAX | STR | STRA | STRB | STRD | STRU |
| 1 | No bacteria infection | − | − | | | | | | | − | | | | |
| 2 | CNS[d] infection | + | + | − | − | − | + | − | − | − | | | | |
| 3 | *S. aureus* infection | + | + | + | − | − | − | − | − | − | | | | |
| 4 | *E. coli* infection | + | − | | | | | | | − | | | | |
| 5 | Streptococci infection | + | − | | | | | | | + | − | − | − | + |

[a] standard bacteriological study performed for mastitis diagnosis by a clinical laboratory
[b] for nucleotide sequences for primer pairs see Table I and Table II
[c] EB = eubacterial primer pair, 16-1D/23-1D (see Table I)
[d] CNS = coagulase negative staphylococci

TABLE VI

Inflammation study from mastitis milk samples as determined
by CMT, Fossomatic cell counting and by PCR with the specific
primer pair P1b/P2b described in Table I

| Milk sample No. | CMT value | Fossomatic cell counting (cells/ml) | PCR product relative intensity* |
|---|---|---|---|
| 1 | 1 | 18 000 | 0.045 |
| 2 | 2 | 189 000 | 0.180 |
| 3 | 3 | 479 000 | 0.249 |
| 4 | 4 | 2 530 000 | 0.355 |
| 5 | 5 | 8 468 000 | 0.420 |

CMT = California mastitis test (CMT 1 = <150 000 cells/ml, CMT 2 = 150 000 − 300 000 cells/ml, CMT 3 = 300 000 − 800 000 cells/ml, CMT 4 = 800 000 − 5 million cells/ml, CMT 5 = >5 million cells/ml)
*the amount of the PCR product was measured as a relative intensity of the band in the agarose gel by a densitometer

We claim:

1. A method for diagnosing mastitis comprising the steps of determining the presence of each of the following DNA sequences in a milk sample:

a somatic cell-specific DNA sequence whose presence indicates inflammation;

a mastitis pathogen-specific DNA sequence whose presence indicates infection by said pathogen;

a DNA sequence of at least one antibiotic resistance-encoding gene of a mastitis pathogen whose presence may be used to determine a proper drug therapy to treat mastitis;

wherein the presence of each of said DNA sequences is determined by contacting nucleic acids in said sample with oligonucleotides specifically hybridizing with said DNA sequences and detecting any hybrids formed, thereby providing a diagnosis of mastitis.

2. The method according to claim 1 wherein said oligonucleotides are either primer pairs for amplification by PCR or are hybridization probes.

3. A method according to claim 1 wherein the presence of said DNA sequences is determined by PCR using oligonucleotides comprising about 15 to 25 nucleotides as primer pairs.

4. A method according to claim 1 wherein said DNA sequence of a somatic cell comprises a conserved region of a bovine 18S rRNA gene.

5. A method according to claim 1 wherein said mastitis pathogen-specific DNA sequence comprises the 16S–23S rRNA spacer region of a Streptcoccus or Staphylococcus mastitis bacterium.

6. A method according to claim 5 wherein said mastitis-pathogen-specific DNA sequence comprises any of SEQ ID NO 1 through 11 or the complementary strands thereof.

7. A method according to claim 1 wherein said DNA sequence of said at least one antibiotic-resistance encoding gene comprises the blaZ gene encoding resistance to β-lactam antibiotics.

8. A test kit for use in a method for diagnosing mastitis from a milk sample comprising at least the following oligonucleotides:

an oligonucleotide which specifically hybridizes with a somatic cell-specific DNA sequence;

an oligonucleotide which specifically hybridizes with a mastitis pathogen-specific DNA sequence;

an oligonucleotide which specifically hybridizes with a DNA sequence of an antibiotic resistance-encoding gene of a mastitis pathogen.

9. A test kit according to claim 8 comprising oligonucleotides which specifically hybridize with mastitis pathogen-specific DNA sequences wherein said mastitis pathogen-specific DNA sequences comprise the 16S–23S rRNA spacer region of Streptococcus or Staphylococcus bacteria.

10. A test kit according to claim 8 comprising at least the following primers for PCR amplification:

an oligonucleotide primer pair which specifically hybridizes with a somatic cell-specific DNA sequence;

an oligonucleotide primer pair which specifically hybridizes with a mastitis pathogen-specific DNA sequence;

an oligonucleotide primer pair which specifically hybridizes with a DNA sequence of an antibiotic resistance-encoding gene of a mastitis pathogen.

11. A test kit according to claim 10 comprising primer pairs which specifically hybridize with a conserved DNA sequence of a eukaryotic 18S rRNA gene;

mastitis-pathogen specific DNA sequences comprising the 16S–23S rRNA spacer region of the pathogen;

and DNA sequences of the blaZ gene of a mastitis pathogen.

12. An oligonucleotide specifically hybridizing with a sequence of any of SEQ ID NO 2 to 11 or with a sequence of the complementary strands thereof.

13. An oligonucleotide according to claim 12 selected from SEQ ID NO 14–35.

* * * * *

SEQUENCE LISTING ( 1 ) GENERAL INFORMATION:

( i i i ) NUMBER OF SEQUENCES: 43

( 2 ) INFORMATION FOR SEQ ID NO: 1:

( i ) SEQUENCE CHARACTERISTICS:
        ( A ) LENGTH: 291 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus agalactiae
        ( B ) STRAIN: ATCC 27956

( x i ) SEQUENCE DESCRIPTION: SEQ ID NO: 1:

```
CTAAGGATAA  GGAAACCTGC  CATTTGCGTC  TTGTTTAGTT  TTGAGAGGTC  TTGTGGGGCC    60
TTAGCTCAGC  TGGGAGAGCG  CCTGCTTTGC  ACGCAGGAGG  TCAGCGGTTC  GATCCCGCTA   120
GGCTCCATTG  AATCGAAAGG  TTCAAATTGT  TCATTGAAAA  TTGAATATCT  ATATCAAATT   180
CCACGATCTA  GAAATAGATT  GTAGAAAGTA  ACAAGAAAAT  AAACCGAAAA  CGCTGTGAAT   240
ATTTAATGAG  TTTTCTAGTT  TTAAAGAAAC  TAGGTTAATA  AGGTTAAGTT  A            291
```

( 2 ) INFORMATION FOR SEQ ID NO: 2:

( i ) SEQUENCE CHARACTERISTICS:
        ( A ) LENGTH: 278 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus bovis
        ( B ) STRAIN: ATCC 27960

( x i ) SEQUENCE DESCRIPTION: SEQ ID NO: 2:

```
CTAAGGATAA  ACGGAAGCAC  GTTTGGGTAT  TGTTTAGTTT  TGAGAGGTCT  TGTGGGCCT    60
TAGCTCAGCT  GGGAGAGCGC  CTGCTTTGCA  CGCAGGAGGT  CAGCGGTTCG  ATCCCGCTAG  120
GCTCCATTGA  ATCGAAAGAT  TCAAAGATTG  TCCATTGAAA  ATTGAATATC  TATATCAAAT  180
TCCACGATTC  AAGAAATTGA  ATTGTAGATA  GTAACAAGAA  ATAAACCGAA  AGCGCTGTGA  240
TTTAATGAGT  TTAAGGTCAA  CAGAACCAAA  ATAAGGTT                             278
```

( 2 ) INFORMATION FOR SEQ ID NO: 3:

( i ) SEQUENCE CHARACTERISTICS:
        ( A ) LENGTH: 287 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus dysgalactiae (Lancefield's -continued group C)
        ( B ) STRAIN: ATCC 27957

( x i ) SEQUENCE DESCRIPTION: SEQ ID NO: 3:

| CTAAGGAAAT | GGAACACGTT | AGGGTCGTCT | TATTTAGTTT | TGAGAGGTCT | TGTGGGGCCT | 60 |
| TAGCTCAGCT | GGGAGAGCGC | CTGCTTTGCA | CGCAGGAGGT | CAGCGGTTCG | ATCCCGCTAG | 120 |
| GCTCCATTAG | GATAGAGATA | TCCTAAAAAC | TGTCCATTGA | AAATTGAATA | TCTATATCAA | 180 |
| ATTCCACGAT | CAAGAAATTG | ATTGTACGAA | TAGTAACAAG | AAAATAAACC | GAAAACGCTG | 240 |
| TGAATAATCA | AGAGTTTTTC | TAGTTAAGAT | ATACTAGTAA | AAGATAA | | 287 |

( 2 ) INFORMATION FOR SEQ ID NO: 4:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus uberis
        ( B ) STRAIN: ATCC 27958

( x i ) SEQUENCE DESCRIPTION: SEQ ID NO: 4:

| CTAAGGATAA | GGAACACGTT | GGTTAAGTCT | TATTTAGTTT | TGAGAGGTCT | TGCAAGACGC | 60 |
| AGAGACAAAC | TGTGGGGCCT | TAGCTCAGCT | GGGAGAGCGC | CTGCTTTGCA | CGCAGGAGGT | 120 |
| CAGCGGTTCG | ATCCCGCTAG | GCTCCATAGG | ATACAGTTCA | ACTGAACTTA | ATAGAAGTGA | 180 |
| AGTTTCATTG | TATCTTAGTA | TAGTCCATTG | AAAATTGAAT | ATCTATATCA | AATTCCACGA | 240 |
| TCATGAAAAT | GATTGTAGAA | AAGTAACAAG | AAATAAACCG | AAAAAAAACG | ATAAACGCGA | 300 |
| ACATATTAAA | AAAAATCAAG | AAGGTCTAAG | GACTGGAAAT | AA | | 342 |

( 2 ) INFORMATION FOR SEQ ID NO: 5:

( i ) SEQUENCE CHARACTERISTICS:
        ( A ) LENGTH: 460 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus aureus subsp. aureus
        ( B ) STRAIN: ATCC 25923

( x i ) SEQUENCE DESCRIPTION: SEQ ID NO: 5:

| CTAAGGATAT | ATTCGGAACA | TCTTCTTCAG | AAGATGCGGA | ATAACGTGAC | ATATTGTATT | 60 |
| CAGTTTTGAA | TGTTTATTTA | ACATTCAAAA | AATGGGCCTA | TAGCTCAGCT | GGTTAGAGCG | 120 |
| CACGCCTGAT | AAGCGTGAGG | TCGGTGGTTC | GAGTCCACTT | AGGCCCACCA | TTATTTGTAC | 180 |
| ATTGAAAACT | AGATAAGTAA | GTAAAATATA | GATTTACCA | AGCAAAACCG | AGTGAATAAA | 240 |
| GAGTTTTAAA | TAAGCTTGAA | TTCATAAGAA | ATAATCGCTA | GTGTTCGAAA | GAACACTCAC | 300 |
| AAGATTAATA | ACGTGTTTAA | ATCTTTTAT | AAAATAAAC | GTTTAGCAGA | CAATGAGTTA | 360 |
| AATTATTTTA | AAGCAGAGTT | TACTTATGTA | AATGAGTATT | TAAAATAATG | AAAACGAAGC | 420 |
| CGTATGTTAA | CGTTTGACTT | ATAAAAATGG | TGGAAACATA | | | 460 |

( 2 ) INFORMATION FOR SEQ ID NO: 6:

( i ) SEQUENCE CHARACTERISTICS:
        ( A ) LENGTH: 281 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus chromogenes
        ( B ) STRAIN: ATCC 43764

( x i ) SEQUENCE DESCRIPTION: SEQ ID NO: 6:

```
CTAAGGATAA  TATACGGAAT  ATCGCTTTTA  AGCGATAAGG  AATAACGGAG  ACATATTGTA      60
TTCAGTTTTG  AATGCTCATT  TTCGAGGCAT  TCAACATTGT  ACATTGAAAA  CTAGATAAGT     120
AAGTATAGAT  TTTACCAAGC  AAAACCGAGT  GACAAGCGAA  AAGCTTGAAA  CAAAAATTAT     180
CGCTAGTCGT  CGACAGACSA  CTCACAATAA  TTAATAACTG  GTGGATGTTG  GTTATTGTTT     240
AATTCGAAAG  CCGAATGTAA  ACGATTGCCA  AAACATCAAA  A                          281
```

( 2 ) INFORMATION FOR SEQ ID NO: 7:

( i ) SEQUENCE CHARACTERISTICS:
        ( A ) LENGTH: 264 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus epidermidis
        ( B ) STRAIN: ATCC 12228

( x i ) SEQUENCE DESCRIPTION: SEQ ID NO: 7:

```
CTAAGGATAT  ATTCGGAACA  TCTTCTACGA  AGATGAGGGA  TAACGTGACA  TATTGTATTC      60
AGTTTTGAAT  GTTTATTAAC  ATTCTTTGTA  CATTGAAAAC  TAGATAAGTA  AGTAAGATTT     120
TACCAAGCAA  AACCGAGTGA  ATAGAGTTTT  AAATAAGCTT  GAATTCATAA  ATAATCGCCT     180
AGTGTTCGAA  AGAACACTCA  CAAGATTAAT  AACTAGTTTT  AGCTATTTAT  TTTTAATAAC     240
AATTCAAAAT  ATGGTGGAAA  CATA                                               264
```

( 2 ) INFORMATION FOR SEQ ID NO: 8:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus hyicus
        ( B ) STRAIN: KNS 264/92 (isolated from a clinical sample)

( x i ) SEQUENCE DESCRIPTION: SEQ ID NO: 8:

```
CTAAGGATAA  TATACGGAAT  ATCGCCTTAG  GCATACGGAA  TAACGAAGAC  ATATTGTATT      60
```

-continued

| | | | | | |
|---|---|---|---|---|---|
| CAGTTTTGAA | TGCTCATTTT | GAGGATTCAA | CATTGTACAT | TGAAAACTAG | ATAAGTAAGT | 120
| ATAGATTTTA | CCAAGCAAAA | CCGAGTGACA | AGCGAAAAGC | TTGAAACAAA | AAATTATCGC | 180
| TAGTCGTCGA | CAGCGACTCA | CAATAATTAA | TAACTGGTGG | ATGTTGGTTA | ATGTTTACTT | 240
| CGGATGACAG | ATGTTTTGAA | AACGTTTGTC | AGTCTATGAA | TCGCAAACAA | GAGCGAAGGC | 300
| CGTTACTTCC | GTAAGCAACT | GAGTGATTTG | TGCCGCGATG | AAGCCGAATG | CAAACGATTG | 360
| CCAAAACATC | ATAAA | | | | | 375

(2) INFORMATION FOR SEQ ID NO: 9:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus simulans
        (B) STRAIN: ATCC 11631

(xi) SEQUENCE DESCRIPTION: SEQ ID NO: 9:

| | | | | | |
|---|---|---|---|---|---|
| CTTTCTAAGG | ATATATTCGG | AACAGTTTCG | CAGGAAACTG | AAACGGAATA | ACGTGACATA | 60
| TTGTATTCAG | TTTTGAATGT | TTATTTGAAA | CATTCAACGT | GAGATGGGCC | TATAGCTCAG | 120
| CTGGTTAGAG | CGCACGCCTG | ATAAGCGTGA | GGTCGGTGGT | TCGAGTCCAC | TTAGGCCCAC | 180
| CATTTTGATT | TTTTGTACAT | TGAAAACTAG | ATAAGTAAGT | AAAAAATAGA | TTTTACCAAG | 240
| CAAAACCGAG | TGAATTAGAG | TTTTAAAAGC | TTTATTCATT | TAAATGAATC | GCTAGTAATC | 300
| AATTGCCGAC | GGCAAACGAT | TACTCACAAT | ATTAATAAC | | | 339

(2) INFORMATION FOR SEQ ID NO: 10:

(i) SEQUENCE CHARACTERISTICS:
        (A) LENGTH: 248 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus simulans
        (B) STRAIN: ATCC 11631

(xi) SEQUENCE DESCRIPTION: SEQ ID NO: 10:

| | | | | | |
|---|---|---|---|---|---|
| CTTTCTAAGG | ATATATTCGG | AACAGTTTCG | CAGGAAAYTG | AAACNGGAAT | AACGTGACAT | 60
| ATTGTATTCA | GTTTTGAATG | TTTATTTGAA | ACATTCAAAG | ATTGTACATT | GAAAACTAGA | 120
| TAAGTAAGTA | AAAAATAGAT | TTTACCAAGC | AAAACCGAGT | GAATTAGAGT | TTTAAAAGCT | 180
| TTATTCATTT | AAATGAATCG | CTAGTAATCA | ATTGCCGACG | GCAAACGATT | ACTCACAATA | 240
| TTAATAAC | | | | | | 248

(2) INFORMATION FOR SEQ ID NO: 11:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (v i) ORIGINAL SOURCE:
    (A) ORGANISM: Staphylococcus xylosus
    (B) STRAIN: ATCC 12162

(x i) SEQUENCE DESCRIPTION: SEQ ID NO: 11:

| | | | | | | |
|---|---|---|---|---|---|---|
| CTAAGGATAT | ATTCGGAACA | TCTTCTTTAG | AAGATGACAG | AGGAATAACA | TTGACATATT | 60 |
| GTATTCAGTT | TTGAATGCTC | ATTGGAGTAT | TCAGTGCATA | ATTTGTACAT | TGAAAACTAG | 120 |
| ATAAGTAAGT | AAAATATATA | GATTTTACCA | AGAAAAACCG | AGTGAATTAG | AGTTTTAAAT | 180 |
| AAGCTTGAAT | TCAAAAGAA | ATAATCGCTA | GTGTTCGAAA | GAACACTCAC | AGATTAATAA | 240 |
| CATTTTGGGT | TTTTAACCGA | CTTCGTCGTG | TTAAAAGTCA | AAAAA | | 285 |

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Streptococcus agalactiae
        (B) STRAIN: ATCC 27956

(x i) SEQUENCE DESCRIPTION: SEQ ID NO: 12:

GGAAACCTGC CATTTGCG        18

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Streptococcus agalactiae
        (B) STRAIN: ATCC 27956

(x i) SEQUENCE DESCRIPTION: SEQ ID NO: 13:

TAACTTAACC TTATTAACCT AG        22

(2) INFORMATION FOR SEQ ID NO: 14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Streptococcus bovis
        (B) STRAIN: ATCC 27960

( x i ) SEQUENCE DESCRIPTION: SEQ ID NO: 14:

GGAAGCACGT TTGGGTATT 19

( 2 ) INFORMATION FOR SEQ ID NO: 15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus bovis
        ( B ) STRAIN: ATCC 27960

( x i ) SEQUENCE DESCRIPTION: SEQ ID NO: 15:

AACCTTATTT TGGTTCTGTT G 21

( 2 ) INFORMATION FOR SEQ ID NO: 16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus dysgalactiae (Lancefield's
            Group C)
        ( B ) STRAIN: ATCC 27957

( x i ) SEQUENCE DESCRIPTION: SEQ ID NO: 16:

TGGAACACGT TAGGGTCG 18

( 2 ) INFORMATION FOR SEQ ID NO: 17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Streptococcus dysgalalactiae (Lancefield's
            Group C)
        ( B ) STRAIN: ATCC 27957

( x i ) SEQUENCE DESCRIPTION: SEQ ID NO: 17:

CTTTTACTAG TATATCTTAA CTA 23

( 2 ) INFORMATION FOR SEQ ID NO: 18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Streptococcus uberis
    ( B ) STRAIN: ATCC 27958

( x i ) SEQUENCE DESCRIPTION: SEQ ID NO: 18:

TAAGGAACAC GTTGGTTAAG 20

( 2 ) INFORMATION FOR SEQ ID NO: 19:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Streptococcus uberis
    ( B ) STRAIN: ATCC 27958

( x i ) SEQUENCE DESCRIPTION: SEQ ID NO: 19:

TCCAGTCCTT AGACCTTCT 19

( 2 ) INFORMATION FOR SEQ ID NO: 20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus aureus subsp. aureus
    ( B ) STRAIN: ATCC 25923

( x i ) SEQUENCE DESCRIPTION: SEQ ID NO: 20:

TCTTCAGAAG ATGCGGAATA 20

( 2 ) INFORMATION FOR SEQ ID NO: 21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus aureus subsp. aureus
    ( B ) STRAIN: ATCC 25923

( x i ) SEQUENCE DESCRIPTION: SEQ ID NO: 21:

TAAGTCAAAC GTTAACATAC G 21

( 2 ) INFORMATION FOR SEQ ID NO: 22:

( i ) SEQUENCE CHARACTERISTICS:
    ( A ) LENGTH: 20 base pairs
    ( B ) TYPE: nucleic acid
    ( C ) STRANDEDNESS: single (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus chromogenes
        (B) STRAIN: ATCC 43764

(xi) SEQUENCE DESCRIPTION: SEQ ID NO: 22:

ACGGAATATC GCTTTTAAGC                                                                                           20

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus chromogenes
        (B) STRAIN: ATCC 43764

(xi) SEQUENCE DESCRIPTION: SEQ ID NO: 23:

CGTTTACATT CGGCTTTCG                                                                                            19

(2) INFORMATION FOR SEQ ID NO: 24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus epidermidis
        (B) STRAIN: ATCC 12228

(xi) SEQUENCE DESCRIPTION: SEQ ID NO: 24:

TCTACGAAGA TGAGGGATA                                                                                            19

(2) INFORMATION FOR SEQ ID NO: 25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus epidermidis
        (B) STRAIN: ATCC 12228

(xi) SEQUENCE DESCRIPTION: SEQ ID NO: 25:

TTTCCACCAT ATTTTGAATT GT                                                                                        22

(2) INFORMATION FOR SEQ ID NO: 26:

-continued ( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus hyicus
    ( B ) STRAIN: KNS 264/92 (isolated from a clinical sample)

( x i ) SEQUENCE DESCRIPTION: SEQ ID NO: 26:

TACGGAATAT CGCCTTAGG      19

( 2 ) INFORMATION FOR SEQ ID NO: 27:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus hyicus
    ( B ) STRAIN: KNS 264/92 (isolated from a clinical sample)

( x i ) SEQUENCE DESCRIPTION: SEQ ID NO: 27:

AAAACATCTG TCATCCGAAG      20

( 2 ) INFORMATION FOR SEQ ID NO: 28:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus simulans
    ( B ) STRAIN: ATCC 11631

( x i ) SEQUENCE DESCRIPTION: SEQ ID NO: 28:

CTTTCTAAGG ATATATTCGG      20

( 2 ) INFORMATION FOR SEQ ID NO: 29:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Staphylococcus simulans
    ( B ) STRAIN: ATCC 11631

( x i ) SEQUENCE DESCRIPTION: SEQ ID NO: 29:

ATTGTGAGTA ATCGTTTGCC      20

( 2 ) INFORMATION FOR SEQ ID NO: 30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus xylosus
        ( B ) STRAIN: ATCC 12162

( x i ) SEQUENCE DESCRIPTION: SEQ ID NO: 30:

TCTTTAGAAG ATGACAGAGG 20

( 2 ) INFORMATION FOR SEQ ID NO: 31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Staphylococcus xylosus
        ( B ) STRAIN: ATCC 12162

( x i ) SEQUENCE DESCRIPTION: SEQ ID NO: 31:

TGACTTTTAA CACGACGAAG 20

( 2 ) INFORMATION FOR SEQ ID NO: 32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Streptococcus sp.

( x i ) SEQUENCE DESCRIPTION: SEQ ID NO: 32:

TGTTTAGTTT TGAGAGGTCT TG 22

( 2 ) INFORMATION FOR SEQ ID NO: 33:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Streptococcus sp.

( x i ) SEQUENCE DESCRIPTION: SEQ ID NO: 33:

CGTGGAATTT GATATAGATA TTC 23

( 2 ) INFORMATION FOR SEQ ID NO: 34:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Staphylococcus sp.

( x i ) SEQUENCE DESCRIPTION: SEQ ID NO: 34:

GGAATAACGT GACATATTGT A    21

( 2 ) INFORMATION FOR SEQ ID NO: 35:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Staphylococcus sp.

( x i ) SEQUENCE DESCRIPTION: SEQ ID NO: 35:

TTCACTCGGT TTTGCTTGG    19

( 2 ) INFORMATION FOR SEQ ID NO: 36:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 36:

GGTGAATACG TTCCCGGG    18

( 2 ) INFORMATION FOR SEQ ID NO: 37:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 37:

CTTACAGCTC CCCAAAGCAT    20

( 2 ) INFORMATION FOR SEQ ID NO: 38:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 38:

GTCGGAATCG CTAGTAATCG    20

( 2 ) INFORMATION FOR SEQ ID NO: 39:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 39:

GGGTTCCCCC ATTCGGA                           17

( 2 ) INFORMATION FOR SEQ ID NO: 40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 40:

AGGAATTCCC AGTAAGTGC                         19

( 2 ) INFORMATION FOR SEQ ID NO: 41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 41:

AGATAGTCAA GTTCGACCG                         19

( 2 ) INFORMATION FOR SEQ ID NO: 42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 42:

GCTCATATTG GTGTTTATGC                         20

( 2 ) INFORMATION FOR SEQ ID NO: 43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 43:

ATCACTATAT GTCATTGAAG C                       21